United States Patent [19]

Konkol et al.

[11] Patent Number: 5,051,522

[45] Date of Patent: Sep. 24, 1991

[54] COMPLEX COMPOUND OF RHODIUM-CONTAINING SULFONATED TRIPHENYLPHOSPHANE

[75] Inventors: Werner Konkol, Oberhausen; Helmut Bahrmann, Hamminkeln; Wolfgang Herrmann, Giggenhausen; Jürgen Kulpe, Frankfurt, all of Fed. Rep. of Germany

[73] Assignee: Hoechst Aktiengesellschaft, Fed. Rep. of Germany

[21] Appl. No.: 632,469

[22] Filed: Dec. 21, 1990

[30] Foreign Application Priority Data

Dec. 23, 1989 [DE] Fed. Rep. of Germany ....... 3942789

[51] Int. Cl.$^5$ ............................................. C07F 15/00

[52] U.S. Cl. ....................................... 556/136; 556/20

[58] Field of Search ...................... 556/136, 13, 19, 20

[56] References Cited

U.S. PATENT DOCUMENTS

| | | | |
|---|---|---|---|
| 4,748,261 | 5/1988 | Billig et al. | ...................... 556/136 X |
| 4,873,213 | 10/1989 | Puckette et al. | ................. 556/136 X |
| 4,885,376 | 12/1989 | Verkade | ........................... 556/136 X |

Primary Examiner—Arthur C. Prescott
Attorney, Agent, or Firm—Jordan B. Bierman

[57] ABSTRACT

Bis{μ-hydroxy)bis[tris(sodium m-sulfonatophenyl)-phosphane]-rhodium(I)} dodecahydrate and methods of preparation thereof. The compounds are useful as catalysts for the hydroformylation reaction.

5 Claims, No Drawings

COMPLEX COMPOUND OF RHODIUM-CONTAINING SULFONATED TRIPHENYLPHOSPHANE

This Application claims the benefit of the priority of German Application P No. 39 42 789.7, filed Dec. 23, 1989.

The invention relates to a new complex compound of rhodium containing, as the complexing ligand, the trisodium salt of tris(m-sulfophenyl)phosphane and a hydroxyl group as further ligands.

BACKGROUND OF THE INVENTION

Complex compounds of a definite composition containing, as one or more ligands, the trisodium salt of triphenylphosphane trisulfonated in the meta position, of the chemical formula $P(C_6H_4\text{-}m\text{-}SO_3Na)_3$, are hardly known. In DE No. 2,700,904 C2, Example 12, the reaction of bis(1,5-cyclooctadiene)nickel with the trisodium salt of tris(m-sulfophenyl)phosphane (hereinafter called TPPTS) is described. A red compound is obtained which is recovered from its aqueous solution as a solid substance by evaporation in vacuo. According to the authors, this compound is supposed to be the tetrakis(trisodium) salt of tetrakis[(m-sulfophenyl)phosphane]-nickel(0).

The same publication also contains general information about the preparation of TPPTS complex compounds of iron and palladium. Thus, water-soluble compounds or those compounds which go into solution under the reaction conditions are to be reacted with aqueous TPPTS solution in the presence of a reducing agent. Examples of suitable reducing agents are $Na[BH_4]$, $K[BH_4]$, zinc powder, magnesium, and borohydrides. Neither the preparation process nor individual compounds are described in more detail by means of examples or even characterized.

Complex compounds containing TPPTS as ligands, the exact composition of which is not known, are formed in various reactions from metals or metal compounds, TPPTS and, if appropriate, further ligands. Thus, rhodium complexes containing TPPTS ligands have achieved particular importance recently as components of catalyst systems which are used in the hydroformylation of olefins. Compared with other catalysts used for the same reaction, they have the advantage of being soluble in water; hence, the hydroformylation can be carried out in a heterogeneous medium comprising an aqueous and an organic phase (two-phase system), as a result of which the reaction product can be separated from the water-soluble catalyst by simple phase separation. Moreover, this procedure ensures that the valuable noble metal catalyst can be recovered almost without loss or be recycled into the synthesis step. Such a process is described, for example, in DE No. 2,627,354 B2.

The addition reaction of hydrogen cyanide with unsaturated organic compounds can also be carried out in the presence of a compound of zero-valent nickel or iron or palladium in a reduced oxidation state and an aqueous solution of a sulfonated triphenylphosphane, in particular an aqueous solution of TPPTS, as catalyst. This procedure is also described in DE No. 2,700,904 C2. Instead of the components nickel salt and TPPTS solution, it is also possible to use a specially prepared complex compound as the catalyst, to which the formula $Ni(TPPTS)_4$ is assigned.

BRIEF DESCRIPTION OF THE INVENTION

The present invention relates to a new TPPTS-containing complex of rhodium; more specifically, the chemical compound $\{(\mu\text{-}OH)Rh[P(C_6H_4\text{-}m\text{-}SO_3Na)_3]_2\}_2$. The new compound is a crystalline, red-brown substance, is soluble in water without decomposition, and can be isolated from its aqueous solution in the form of a hydrate. This hydrate contains one molecule of water per sodium ion. At room temperature, the compound is stable in air.

DETAILED DESCRIPTION OF THE INVENTION

The compound claimed can be prepared by various methods. One proven synthesis starts with chlorotris[tris(sodium m-sulfonatophenyl)phosphane]-rhodium(I) nonahydrate $(ClRh(TPPTS)_3\cdot 9H_2O)$, which is obtained, for example, by reaction of $RhCl_3\cdot 3H_2O$ with TPPTS. The complex compound purified by gel permeation chromatography is treated with hydrazine hydrate in aqueous solution. The reaction is carried out at room temperature or slightly elevated temperature. The hydrazine hydrate is usually used in a stoichiometric ratio.

According to a different method, the complex $HRh[P(C_6H_5)_3]_4$, which is known from the literature, is reacted in a two-phase system (for example methylene chloride/water) with excess TPPTS, resulting in the formation of elemental hydrogen. In this reaction, the complex $(OH)Rh(TPPTS)_3$ is also formed; this complex is obtained by treating $RhCl_3\cdot 3H_2O$ in aqueous solution with excess TPPTS at room temperature over a period of more than 15 hours.

To isolate the new compound which, regardless of the method of preparation, is present in aqueous solution, the water is evaporated in vacuo, if necessary after filtration of the solution. In general, this method does not give the pure compound, but an impure product or even a mixture of various TPPTS complex compounds which have been formed side by side during the preparation. It is therefore necessary to apply special purification and separation processes, in order to obtain the pure substance. It has been proven that gel chromatography, which is the subject matter of German patent application P No. 38 22 036.9, is a particularly suitable method for achieving this object. After this treatment, the compound is present in analytical and spectroscopic purity.

The new compound crystallizes from the aqueous solution in the form of a hydrate. The anhydrous compound can be prepared therefrom by dehydration under mild conditions, i.e. at temperatures below the melting or decomposition point and by applying reduced pressure, advantageously high vacuum, without decomposition. The protection claimed therefore extends, not only to the water-containing compound but also to the anhydrous TPPTS complex. The compound according to the invention is catalytically active and is used successfully as catalyst or component of catalysts in various reactions.

The invention is illustrated in more detail in the example which follows.

Synthesis of bis{(μ-hydroxy)bis[tris(sodium m-sulfonatophenyl)phosphane]rhodium(I)} dodecahydrate of the formula {(μ-OH)Rh[P($C_6H_4$-m-$SO_3Na$)$_3$]$_2$}$_2$.12 $H_2O$ 5 ml (5.15 g, 0.102 mol) of hydrazine hydrate are added to a solution of 250 mg (0.13 mmol) of ClRh(TPPTS)$_3$.9$H_2O$ in 20 ml of distilled water, and the mixture is stirred at room temperature for 48 hours. The solvent is then completely removed under vacuum produced by an oil pump. The solid residue is taken up in 10 ml of water and purified by column chromatography over Sephadex G-15 (dextranes crosslinked with epichlorohydrin). The product is detected by UV/VIS spectrometry and refractometry.

Yield: 140 mg (79%); red-brown glass.

Characterization $^{31}$P-NMR (109.3 MHz, $D_2O$, 21° C.): δ=58.9 ppm [d]; $^1$J(Rh,P) =203 Hz IR (KBr, $cm^{-1}$): 1635 (m), 1464 (m), 1396 (m), 1192 (sh, vs), 1037 (s).

Elemental analysis: ($C_{72}H_{72}Na_{12}O_{50}P_4Rh_2S_{12}$; 2729.6): Calculated: C 31.58 H 2.73 Cl 0.0 O 29.31, P 4.53, Rh 7.53 S 14.09; Found: C 32.35 H 2.62, Cl 0.0 O29.57, P 4.33 Rh, 7.20 S 14.42.

What we claim is

1. Bis{(μ-hydroxy)bis[tris(sodium m-sulfonatophenyl)-phosphane]rhodium(I)} dodecahydrate.

2. A process for the preparation of the compound of claim 1 which comprises reacting ClRh[P($C_6H_4$-m-$SO_3Na$)$_3$].9$H_2O$ in aqueous solution at least at room temperature with hydrazine hydrate to form a reaction product containing said compound.

3. A process for the preparation of the compound of claim 1 which comprises reacting HRh[P($C_6H_5$)]$_4$ with excess P($C_6H_4$-m-$SO_3Na$)$_3$ to form a reaction product containing said compound.

4. The process of claim 2 further comprising purification of said compound by gel chromatography.

5. The process of claim 3 further comprising purification of said compound by gel chromatography.